United States Patent
Okamoto

(10) Patent No.: US 8,609,908 B2
(45) Date of Patent: Dec. 17, 2013

(54) PROCESS FOR PRODUCING 1,1-DICHLORO-2,2,3,3,3-PENTAFLUOROPROPANE

(75) Inventor: Hidekazu Okamoto, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 271 days.

(21) Appl. No.: 13/167,455

(22) Filed: Jun. 23, 2011

(65) Prior Publication Data

US 2012/0004474 A1 Jan. 5, 2012

Related U.S. Application Data

(60) Provisional application No. 61/365,919, filed on Jul. 20, 2010.

(30) Foreign Application Priority Data

Jun. 23, 2010 (JP) .................................. 2010-142278

(51) Int. Cl.
 *C07C 19/08* (2006.01)
(52) U.S. Cl.
 USPC ............................ 570/156; 570/151; 570/176
(58) Field of Classification Search
 None
 See application file for complete search history.

(56) References Cited

U.S. PATENT DOCUMENTS

| | | | |
|---|---|---|---|
| 5,157,171 A | 10/1992 | Sievert et al. | |
| 6,548,719 B1 * | 4/2003 | Nair et al. | 570/157 |
| 8,293,953 B2 * | 10/2012 | Okamoto | 570/151 |
| 2010/0022808 A1 | 1/2010 | Rao et al. | |
| 2010/0185028 A1 | 7/2010 | Okamoto | |

FOREIGN PATENT DOCUMENTS

| | | |
|---|---|---|
| JP | 5-58924 | 3/1993 |
| JP | 8-169850 | 7/1996 |
| JP | 2010-510221 | 4/2010 |
| WO | WO 2010/074254 A1 | 7/2010 |
| WO | WO 2010/082662 A1 | 7/2010 |

OTHER PUBLICATIONS

U.S. Appl. No. 13/167,464, filed Jun. 23, 2011, Takagi, et al.
U.S. Appl. No. 13/167,285, filed Jun. 23, 2011, Seki, et al.
U.S. Appl. No. 13/167,235, filed Jun. 23, 2011, Kawaguchi, et al.
U.S. Appl. No. 13/167,509, filed Jun. 23, 2011, Kawaguchi, et al.
U.S. Appl. No. 13/167,145, filed Jun. 23, 2011, Takagi, et al.
U.S. Appl. No. 13/167,254, filed Jun. 23, 2011, Kawaguchi, et al.
T. Tanuma, et al. "Applied Catalysis A: General", Metal Halide Catalysts to Synthesize Dichloropentafluoropropanes by the Reaction of Dichlorofluoromethane with Tetrafluoroethylene, 348, pp. 236-240, (2008).
International Search Report issued Aug. 9, 2011, in PCT/JP2011/064421 (with Translation of Category of Cited Documents).
T. Tanuma, et al., "Partially Fluorinated Metal Oxide Catalysts for a Friedel-Crafts-type Reaction of Dichlorofluoromethane with Tetrafluoroethylene", Catalysis Letters, vol. 136, May 2010, pp. 77-82.
T. Tanuma, et al., "Activated zirconium oxide catalysts to synthesize dichloropentafluoropropane by the reaction of dichlorofluoromethane with tetrafluoroethylene", Applied Catalysis A: General, vol. 359, 2009, pp. 158-164.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

To provide a process for producing, at a high content ratio, 1,1-dichloro-2,2,3,3,3-pentafluoropropane (HCFC-225ca) which is useful as e.g. a starting material to obtain 1,1-dichloro-2,3,3,3-tetrafluoropropene (CFO1214ya).

The process for producing HCFC-225ca of the present invention comprises subjecting a raw material composed of dichloropentafluoropropane (HCFC-225) including 2,2-dichloro-1,1,1,3,3-pentafluoropropane (HCFC225aa) to an isomerization reaction at a temperature of at most 290° C. in a gas phase in the presence of a metal oxide catalyst thereby to isomerize HCFC-225aa to HCFC-225ca.

11 Claims, No Drawings

US 8,609,908 B2

PROCESS FOR PRODUCING 1,1-DICHLORO-2,2,3,3,3-PENTAFLUOROPROPANE

CONTINUING APPLICATION INFORMATION

This application claims benefit of the filing date of Provisional Application No. 61/365,919, filed on Jul. 20, 2010.

TECHNICAL FIELD

The present invention relates to a process for producing 1,1-dichloro-2,2,3,3,3-pentafluoropropane.

BACKGROUND ART

Heretofore, various methods have been proposed as methods for producing dichloropentafluoropropanes (HCFC-225) represented by a chemical formula $C_3HCl_2F_5$. For example, a method for obtaining dichloropentafluoropropanes by contacting dichlorofluoromethane with tetrafluoroethylene in the presence of a modified aluminum chloride catalyst, has been proposed, and techniques to apply isomerization to a mixture of various isomers of dichloropentafluoropropane obtained by such a method, have been disclosed (e.g. Patent Document 1 and Non-Patent Document 1).

However, the isomerization method disclosed in Patent Document 1 is a method to increase the content ratio of 2,2-dichloro-1,1,1,3,3-pentafluoropropane ($CHF_2CCl_2CF_3$: HCFC-225aa), and by this method, it was not possible to obtain, at a high content ratio, 1,1-dichloro-2,2,3,3,3-pentafluoropropane ($CHCl_2CF_2CF_3$; HCFC-225ca).

Whereas, the method disclosed in Non-Patent Document 1 is a method for synthesizing HCFC-225ca by isomerizing 1,3-dichloro-1,1,2,2,3-pentafluoropropane ($CHClFCF_2CClF_2$: HCFC-225cb) by means of a partially fluorinated aluminum chloride catalyst, and by this method, the yield of HCFC-225ca was as low as about 10%, and the production efficiency was poor. It is conceivable to carry out the reaction for an extended period of time or at a high temperature in order to increase the yield of HCFC-225ca, but in the case of using a fluorinated aluminum halide catalyst, it has been found that if the conversion is increased to increase the yield of HCFC-225ca, compounds other than HCFC-225 isomers are produced in a large amount by halogen exchange with the catalyst or by a disproportionation reaction among various isomers of HCFC-225, such being problematic.

Therefore, by the conventional methods, it has been impossible to efficiently obtain HCFC-225ca which is a starting material for synthesizing 2,3,3,3-tetrafluoropropene ($CF_3CF=CH_2$; HFO-1234yf) as a new refrigerant. That is, in recent years, use of HFO-1234yf having a small ozone destruction coefficient has been studied as a new refrigerant to replace 1,1,1,2-tetrafluoroethane (HFC-134a) as a greenhouse gas, and usefulness of HCFC-225ca has been increasing as a starting material to obtain 1,1-dichloro-2,3,3,3-tetrafluoropropene ($CF_3CF=CCl_2$; CFO-1214ya) which is a raw material for synthesis of such HFO-1234yf. However, a method of increasing the content ratio of HCFC-225ca in the mixture of various isomers of HCFC-225 to obtain HCFC-225ca efficiently, has not been found.

PRIOR ART DOCUMENTS

Patent Document

Patent Document 1: U.S. Pat. No. 5,157,171

Non-Patent Document

Non-Patent Document 1: Applied Catalysis A: General, 348, 236-240 (2008)

DISCLOSURE OF INVENTION

Technical Problem

It is an object of the present invention to provide a process for producing 1,1-dichloro-2,2,3,3,3-penafluoropropane (HCFC-225ca) useful as e.g. a starting material to obtain 1,1-dichloro-2,3,3,3-tetrafluoropropene (CFO-1214ya) which is a raw material for synthesis of 2,3,3,3-tetrafluoropropene (HFO-1234yf) as a new refrigerant having a small ozone depletion potential, etc. Further, it is an object of the present invention to provide a process for producing CFO-1214ya by using HCFC-225ca obtained by such a process.

Solution to Problem

The present invention provides a process for producing 1,1-dichloro-2,2,3,3,3-pentafluoropropane (HCFC-225ca), which comprises reacting a raw material containing 2,2-dichloro-1,1,1,3,3-pentafluoropropane (HCFC-225aa) at a temperature of at most 290° C. in a gas phase in the presence of a metal oxide catalyst thereby to isomerize at least a part of 2,2-dichloro-1,1,1,3,3-pentafluoropropane (HCFC-225aa) in the above raw material to 1,1-dichloro-2,2,3,3,3-pentafluoropropane (HCFC-225ca).

Further, the present invention provides the following process for producing 1,1-dichloro-2,3,3,3-tetrafluoropropene (CFO-1214ya).

A process for producing CFO-1214ya, which comprises reacting dichloropentafluoropropane containing HCFC-225ca and HCFC-225aa to a dehydrofluorination reaction in an alkali aqueous solution in the presence of a phase-transfer catalyst to produce CFO-1214ya from HCFC-225ca, then separating CFO-1214ya from the dehydrofluorination reaction product, reacting dichloropentafluoropropane including HCFC-225aa after separating CFO-1214ya, at a temperature of at most 290° C. in a gas phase in the presence of a metal oxide catalyst, to isomerize a part of HCFC-225aa in the dichloropentafluoropropane to HCFC-225ca thereby to produce dichloropentafluoropropane including HCFC-225ca and HCFC-225aa, and repeating the above process to produce CFO-1214ya from the obtained dichloropentafluoropropane.

Advantageous Effect of Invention

According to the present invention, it is possible to obtain, at a high content ratio (molar ratio), 1,1-dichloro-2,2,3,3,3-pentafluoropropane (HCFC-225ca) useful as a starting material to synthesize 2,3,3,3-tetrafluoropropene (HFO-1234yf) as a new excellent refrigerant.

DESCRIPTION OF EMBODIMENT

In the following description, one of the compounds represented by $C_3HCl_2F_5$, or a mixture of two or more of them (a mixture of compounds which are isomers to one another) is referred to as dichloropentafluoropropane and is referred to also as HCFC-225.

Further, one composed solely of a specific compound X represented by $C_3HCl_2F_5$, or a mixture composed of the compound X and at least one of its isomers, is referred to as dichloropentafluoropropane including the compound X. A mixture of the specific compound represented by $C_3HCl_2F_5$ and only a specific compound Y being an isomer of the compound X, or a mixture of the compound X, the compound Y and at least one of their isomers, is referred to as dichloropentafluoropropane including the compound X and the compound Y.

The process according to the embodiment of the present invention is characterized in that HCFC-225 containing HCFC-225aa is used as a raw material, and this raw material is subjected to an isomerization reaction in a gas phase in the presence of a metal oxide as a catalyst to isomerize at least a part of HCFC-225aa in the raw material to HCFC-225ca. The content ratio of HCFC-225ca in HCFC-225 as the raw material may be 0 mol %.

In the embodiment of the present invention, by side-reactions of the isomerization reaction, the isomerization reaction product may contain hydrochlorofluorocarbon compounds in addition to HCFC-225. However, their amount can be made very small at a level of less than 10 mol % based on the total amount with dichloropentafluoropropane in the reaction product. Here, the hydrochlorofluorocarbon compounds other than HFCF-225 include, for example, trichlorotetrafluoropropanes (HCFC-224) and monochlorohexafluoropropanes (HCFC-226). More specifically, HCFC-224 may, for example, be 1,2,2-trichloro-1,3,3,3-tetrafluoropropane (HCFC-224aa) or 1,1,2-trichloro-2,3,3,3-tetrafluoropropane (HCFC-224ba). Further, HCFC-226 may, for example, be 1-chloro-1,1,2,2,3,3-hexafluoropropane (HCFC-226cb).

In the embodiment of the present invention, as the raw material for the isomerization reaction, it is possible to employ any material so long as it is HCFC-225 containing HCFC-225aa, but it is preferred to use HCFC-225 which contains, in addition to HCFC-225aa, 1,3-dichloro-1,2,2,3,3-pentafluoropropane (HCFC-225cb). Further, it is preferred to use HCFC-225, wherein the content ratio of HCFC-225ca is less than 50 mol %. Further, as the raw material for the isomerization reaction, it is possible to use for example, HCFC-225 including HCFC-225cb and HCFC-225aa formed in the process for producing 2,3,3,3-tetrafluoropropene (HFO-1234yf) as a new refrigerant.

In a case where HCFC-225 including HCFC-225aa is used as the raw material (i.e. excluding the after-described case where HCFC-225 including HCFC-225aa and HCFC-225cb is used as the raw material), the proportion of HCFC-225aa based on the total amount of HCFC-225 is preferably at least 50 mol %, more preferably at least 70 mol %. However, the content of HCFC-225cb is less than 5 mot % based on the total amount of CFC-225aa and HCFC-225cb. Further, the content of HCFC-225 other than HCFC-225aa (other than HCFC-225cb) is preferably less than 50 mol %, more preferably less than 30 mol %, based on the total amount of HCFC-225.

In a case where HCFC-225 as the raw material for the isomerization reaction contains HCFC-225cb in addition to HCFC-225aa, at least a part of HCFC-225cb is also isomerized under the isomerization reaction conditions in the present invention. Accordingly, in a case where HCFC-225 including HCFC-225aa and HCFC-225cb is used as the raw material, HCFC-225ca in the reaction product is considered to be composed of one formed by isomerization of HCFC-225aa and one formed by isomerization of HCFC-225cb.

In a case where HCFC-225 including HCFC-225aa and HCFC-225cb is used as the raw material, the amount of HCFC-225aa based on the total amount of HCFC-225 is preferably at least 30 mol %, more preferably at least 50 mol %. The amount of HCFC-225cb based on the total amount of HCFC-225 is preferably at most 70 mol %, more preferably at most 50 mol %. Further, the content of HCFC-225 other than HCFC-225aa and HCFC-225cb is preferably less than 50 mol %, more preferably less than 30 mol %, based on the total amount of HCFC-225. Here, in the raw material, HCFC-225 including HCFC-225aa and HCFC-225cb means that the amount of HCFC-225cb is at least 5 mol % based on the total amount of CFC-225aa and HCFC-225cb.

As HCFC-225 including HCFC-225aa and HCFC-225cb, it is possible to use the following HCFC-225 formed in a process for producing HFO-1234yf.

That is, in order to form 1,1-dichloro-2,3,3,3-tetrafluoropropene (CFO-1214ya) as a raw material for synthesis of HFO-1234yf, HCFC-225 including HCFC-225ca is contacted with an alkali aqueous solution in the presence of a phase-transfer catalyst so that HCFC-225ca is selectively subjected to a dehydrofluorination reaction.

HCFC-225 as the starting material for this reaction contains, in addition to HCFC-225ca, HCFC-225cb, HCFC-225aa, etc., and such HCFC-225cb, HCFC-225aa, etc. will remain as they are without being reacted (dehydrofluorinated). HCFC-225 including the remaining HCFC-225cb, HCFC-225aa, etc. can easily be separated from formed CFO-1214ya by distillation, and HCFC-225 including HCFC-225cb, HCFC-225aa, etc., thus separated from CFO-1214ya, can be used as a raw material for the isomerization reaction of the present invention.

Further, as the raw material for the isomerization reaction of the present invention, it is also possible to use HCFC-225 obtainable via the following process. That is, in a case where as HCFC-225 to be subjected to dehydrofluorination, HCFC-225 comprising HCFC-225ca, HCFC-225cb and their isomers, which commercialize as ASAHIKLIN AK225 (tradename, manufactured by Asahi Glass Company, Limited), is used, a residue recovered after removing CFO-1214ya by distillation that formed by the dehydrofluorination reaction, becomes HCFC-225 containing HCFC-225cb as the main component. And, a product obtainable by an isomerization reaction using such a residue as the raw material becomes HCFC-225 containing HCFC-225ca and HCFC-225aa as the main components, and therefore, when such a mixture is further subjected to a dehydrofluorination reaction, a residue recovered after removing by distillation CFO-1214ya thereby formed, becomes HCFC-225 containing HCFC-225aa as the main component.

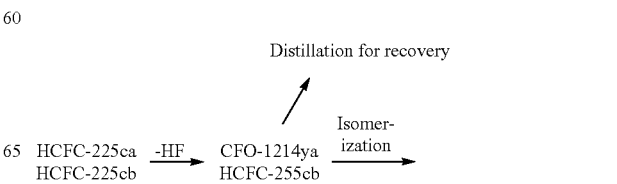

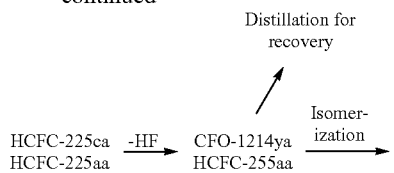

In the embodiment of the present invention, HCFC-225 containing HCFC-225aa as the main component can be used as the raw material for the isomerization reaction. Thus, by carrying out the isomerization reaction, it is possible to improve the content ratio of HCFC-225ca in HCFC-225 containing HCFC-225aa as the main component, as the raw material. And, by repeating such an operation, it becomes possible to form HCFC-225ca in very good yield.

That is, by repeating the isomerization of HCFC-225aa to HCFC-225ca, the dehydrofluorination of HCFC-225ca and the separation of the formed CFO-1214ya, it becomes possible to form HCFC-225ca from HCFC-225aa in a very high yield. Further, in such repetition, by adding separately produced HCFC-225cb to HCFC-225aa, it becomes possible to consequently form HCFC-225ca in high yield from HCFC-225cb.

Further, by repeating the isomerization of HCFC-225aa to HCFC-225ca, the dehydrofluorination of HCFC-225ca and the separation of the formed CFO-1214ya, it becomes possible to consequently form CFO-1214ya in high yield from HCFC-225aa. Further, to this repeating reaction system, it is possible to add HCFC-225aa obtained by a separate reaction (for example, HCFC-225aa formed as a by-product in the isomerization of HCFC-225cb to HCFC-225ca). Further, it is possible to carry out the reaction by adding HCFC-225cb to HCFC-225aa in this repeating reaction system. Thus, consequently, it is possible to form CFO-1214ya in high yield from HCFC-225cb.

In the embodiment of the present invention, the catalyst to be used for the isomerization reaction in a gas phase is not particularly limited so long as it is a metal oxide, but it is preferably an oxide of at least one element selected from the group consisting of Al, Sb, Nb, Ta, W, Re, B, Sn, Ga, In, Zr, Hf and Ti. From the viewpoint of the reaction activity and selectivity, an aluminum oxide type catalyst is preferred as the metal oxide catalyst. Further, as the metal oxide catalyst, a preliminarily activated metal oxide catalyst may be used, and as such a preliminarily activated metal oxide catalyst, a partially fluorinated metal oxide catalyst is preferred. As such a partially fluorinated metal oxide catalyst, a partially fluorinated aluminum oxide catalyst is preferred. The partially fluorinated metal oxide catalyst can be produced by partially fluorinating a metal oxide, for example, by contacting a metal oxide with a gas of a fluorinated compound (e.g. a fluorocarbon such as Freon) at a high temperature.

In the isomerization reaction in a gas phase, the reaction temperature is at most 290° C., preferably from 150 to 290° C., more preferably from 180 to 250° C. In order to maximize the yield of the desired product HCFC-225ca, it is preferred to finely control the reaction temperature depending upon the ratios of various HCFC-225 in the raw material to be used. Such fine control of the reaction temperature is required, because the reactivity for the isomerization reaction varies depending upon the type of HCFC-225, and a halogen exchange reaction (disproportionation reaction) among isomer molecules will proceed via the catalyst. In order to improve the conversion of the raw material, it is preferred to carry out the reaction at a higher temperature, but if the temperature is too high, a disproportionation reaction tends to proceed among isomer molecules, thereby to increase formation of byproducts (e.g. HCFC-224, HCFC-226, etc.) other than HCFC-225, which cannot be recycled for the desired HCF-225ca, such being undesirable.

In the embodiment of the present invention, by adjusting the reaction temperature for isomerization in the gas phase to be at most 290° C., it is possible to bring the amount of hydrochlorofluorocarbon compounds other than HCFC-225 formed as by-products, to be less than 10 mol %.

For example, as mentioned above, in a case where ASAHIKLIN AK225 is subjected to a dehydrofluorination reaction in the presence of an alkali, then HCFC-225cb remaining after distillation and recovery of CFO-1214ya thereby formed, is subjected, as a raw material, to an isomerization reaction to obtain HCFC-225 containing HCFC-225ca and HCFC-225aa, which is again subjected to a dehydrofluorination reaction in the presence of an alkali, and a residue (HCFC-225 containing HCFC-225aa as the main component) after distillation and recovery of CFO-1214ya thereby formed, is subjected, as a raw material, to isomerization, if the reaction temperature exceeds 290° C., the amount of byproducts such as HCFC-224 and HCFC-226 formed by a disproportionation reaction increases, such being undesirable. In a case where such HCFC-225 including HCFC-225aa is used as a raw material, it is preferred to set an optimum reaction temperature by taking the ratios of the respective isomers into consideration.

In the isomerization reaction in the gas phase, the reaction pressure is preferably within a range of from 0 to 2 kg/cm², particularly-preferably within a range of from 0 to 1 kg/cm². The reaction time is usually from 10 to 180 seconds, preferably from 20 to 90 seconds, although it depends also on the reaction temperature or the type of the metal oxide catalyst. In the isomerization reaction, the raw material may be diluted with an inert gas such as nitrogen and then supplied to the reaction. The molar ratio of the raw material to the inert gas is preferably from 1:0.1 to 1:10, more preferably from 1:0.1 to 1:5.

In the embodiment of the present invention, it is possible to form HCFC-225ca by subjecting HCFC-225 including HCFC-225aa, as a raw material, to an isomerization reaction in a gas phase in the presence of the above-described metal oxide catalyst under the above-described reaction conditions, and it is possible to bring the content ratio of HCFC-225ca in the reaction product to be substantially higher than the content ratio in the raw material.

Especially in a case where the raw material is HCFC-225 containing both HCFC-225aa and HCFC-225cb, HCFC-225ca will be formed by the isomerization reactions of HCFC-225aa and HCFC-225cb, whereby the content ratios (molar ratios) of HCFC-225cb and HCFC-225aa in the raw material will decrease, and, instead, the content ratio of HCFC-225ca will increase as compared with the content ratio in the raw material.

Here, in order to let HCFC-225ca be formed by the isomerization reaction and to bring the content ratio of HCFC-225ca in the reaction product to be higher than the content ratio in the raw material, it is preferred to adjust the content ratio of HCFC-225ca in the raw material to be less than 50 mol %, for the following reason.

That is, in a case where HCFC-225aa alone (which may further contain 225ca) or a mixture of HCFC-225aa and HCFC-225cb (which may further contain 225ca) is subjected to an isomerization reaction, for example, at 25° C., the content ratio of HCFC-225ca in the equilibrium state becomes from 78 to 80 mol % based on the total amount of HCFC-225.

The value of this content ratio decreases if the reaction temperature becomes high, but such a value will not be less than 60 mol %. Accordingly, if the content ratio of HCFC-225ca in the raw material is higher than 60 mol % (e.g. 70 mol %) based on the total amount of HCFC-225, there may be a case where by the isomerization reaction, the content ratio of HCFC-225ca becomes lower than the content ratio in the raw material, but if the content ratio of HCFC-225ca is less than 60 mol %, the content ratio of HCFC-225ca in the reaction product necessarily becomes higher than the content ratio in the raw material. That is, by the isomerization reaction of the raw material, HCFC-225ca will be formed, and its content ratio can be made higher than in the raw material. In a real reaction, disproportionation products other than HCFC-225, or byproducts such as decomposed products may be formed, and when such a situation and the yield in a distillation step are taken into consideration, it is preferred to adjust the concentration of HCFC-225ca in the raw material to be less than 50 mol % based on the total amount of HCFC-225. And, it is preferred to carry out the isomerization by using such a raw material under such reaction conditions that by the isomerization, the content ratio of HFCF-225ca is brought to be higher by at least 15 mol % than the content ratio in the raw material.

Thus, according to the embodiment of the present invention, it is possible to obtain HCFC-225ca at a high content ratio in HCFC-225. And, HCFC-225ca thereby obtained can be used as a starting material to form CFO-1214ya.

In order to produce CFO-1214ya by using HCFC-225 including HCFC-225ca as a starting material, it is possible to employ, for example, a method of selectively dehydrofluorinating only HCFC-225ca by contacting the starting material with an alkali aqueous solution in the presence of a phase-transfer catalyst. Here, the alkali aqueous solution is not particularly limited so long as it is an aqueous solution of a basic compound capable of carrying out the dehydrofluorination reaction, but it is preferred to employ an aqueous solution of e.g. sodium hydroxide or potassium hydroxide. The alkali concentration in the alkali aqueous solution is not particularly limited, but it is preferred to adjust it so that the alkali amount will be from 0.5 to 1.5 mol equivalent, more preferably from 0.8 to 1.2 mol equivalent, to the amount of HCFC-225ca to be used for the reaction. On the other hand, as the phase-transfer catalyst, a commonly employed phase-transfer catalyst may be used without any particularly restriction. Specifically, it is possible to use e.g. a quaternary ammonium salt or quaternary phosphonium salt substituted by a hydrocarbon group, or a crown ether. The amount of the phase-transfer catalyst is preferably an amount of from 0.001 to 5 mass %, more preferably from 0.01 to 1 mass %, to the mass of HCFC-225ca as the raw material. Further, the reaction temperature in the above dehydrofluorination reaction is not particularly limited, but it is preferably within a range of from 0 to 80° C., more preferably within a range of from 0 to 50° C.

CFO-1214ya thus obtained is further reacted with hydrogen in the presence of a catalyst (e.g. Pd catalyst) to obtain HFO-1234yf which is a new excellent refrigerant to replace a greenhouse gas.

EXAMPLES

Now, the present invention will be described in detail with reference to Examples, but it should be understood that the present invention is by no means restricted by these Examples.

Reference Example

An isomerization reaction of HCFC-225cb was carried out by using a Lewis acid catalyst. Firstly, a Lewis acid catalyst was prepared as shown below. That is, a Dimroth condenser to circulate a cooling medium cooled to −20° C. was attached to a three-necked flask (internal capacity: 1,000 mL), and 100 g of aluminum trichloride ($AlCl_3$) was charged into the flask and cooled to 0° C., and then, 1,000 g (7.3 mol) of trichlorofluoromethane ($CFCl_3$) was slowly dropwise added with stirring.

Along with generation of a low boiling point gas, a disproportionation reaction of trichlorofluoromethane proceeded. And, along with the progress of the disproportionation reaction, a halogen exchange reaction between aluminum trichloride ($AlCl_3$) as the catalyst and trichlorofluoromethane as the substrate proceeded to form a fluorinated aluminum halide. After continuing the reaction at 0° C. for 12 hours, a volatile component was removed, and the catalyst was dried thereby to obtain a partially fluorinated aluminum chloride.

Then, into a glass reactor (internal capacity: 1 L) provided with a Dimroth condenser cooled to 0° C., 90 g of the partially fluorinated aluminum chloride obtained by the above reaction was put as a catalyst, and 609 g (3.0 mol) of 1,3-dichloro-1,1,2,2,3-pentafluoropropane (HCFC-225cb) was added thereto.

Then, the temperature in the reactor was raised to 50° C., and the reaction was carried out for 100 hours with stirring. A liquid after the reaction was filtrated to remove the catalyst and to recover 580 g of a product. The obtained product was analyzed by means of gas chromatography to determine the composition. The results are shown in Table 1.

TABLE 1

|  |  | Raw material | Reaction product |
|---|---|---|---|
| HCFC-225 (mol %) |  | 100 | 80 |
| Other than HCFC-225 (mol %) | HCFC-226cb | 0 | 5 |
|  | HCFC-224aa | 0 | 3 |
|  | HCFC-224ba | 0 | 10 |
|  | Other compounds | 0 | 2 |
| Composition of HCFC-225 (mol %) | HCFC-225cb | 99.9 | 0 |
|  | HCFC-225ca | 0 | 70 |
|  | HCFC-225aa | 0 | 26 |
|  | Other 225 compounds | 0.1 | 4 |

From Table 1, it was found that when the isomerization reaction of HCFC-225cb as the raw material was completed by using the fluorinated aluminum halide catalyst as a Lewis acid catalyst, the amount of byproducts (e.g. HCFC-226, HCFC-224) other than HFCF-225 isomers increased, and the recovered amount of the product decreased to 580 g relative to 609 g of the raw material (HCFC-225cb). It is considered that such results were caused by a halogen exchange reaction (disproportionation reaction) proceeded among HCFC-225 molecules as a side reaction and a halogen exchange reaction proceeded between HCFC-225 and an aluminum halide used as the catalyst. Further, since the boiling point of HCFC-226 is low, a decrease in yield caused by a loss due to vaporization of HCFC-226 is also assumed.

Examples 1 to 6 and Comparative Example

Firstly, a metal oxide catalyst was prepared as follows. That is, a catalyst of spherical active alumina (tradename: ACBM-1, manufactured by Catalysts & Chemicals Industries Co., Ltd., specific surface area: 280 m$^2$/g) having a particle size of 2 mm was packed into a reaction tube made of Inconel (registered trademark) 600 having an inner diameter of 2.54 cm and a length of 100 cm, and immersed in a salt bath. The reaction tube was heated to 250° C., and a mixed gas of nitrogen/freon R-12 ($CCl_2F_2$) being 2/1 (molar ratio) was permitted to flow through for 4 hours at a contact time of 20 seconds thereby to partially fluorinate and activate the catalyst.

Then, as a raw material, HCFC-225 including HCFC-225aa was prepared as follows. Firstly, into a glass reactor having an internal capacity of 1 L provided with a Dimroth condenser cooled to 0° C., 0.5 g of tetrabutylammonium bromide (TBAB) as a phase-transfer catalyst, 83 g of potassium hydroxide, 124 g of water and 609 g of ASAHIKLIN AK225 (mixture of HCFC-225ca, HCFC-225cb and other HCFC-225 isomers) were charged, and then, a reaction was carried out at 20° C. for 5 hours with stirring to selectively dehydrofluorinate HCFC-225ca. The reaction crude liquid thus obtained was subjected to liquid separation, and then, the organic phase was distilled to recover CFO-1214ya (boiling point: 45° C.). As a residue after the recovery, HCFC-225 containing at least 95% of HCFC-225cb was obtained.

Then, this HCFC-225 was permitted to flow in the reaction tube packed with the partially fluorinated aluminum oxide under such conditions that the raw material supplied ratio (HCFC-225/nitrogen) was 1/2 (molar ratio), the reaction temperature was 300° C. and the contact time was 20 seconds to carry out an isomerization reaction. The reaction was continued for 10 hours, and then the gas composition at the outlet of the reactor was analyzed by gas chromatography, whereby an isomerized crude liquid having the composition shown in Table 2 was obtained. Here, "Other compounds" in the section for "Other than HCFC-225" represent fluorinated compounds other than HCFC-225 and other than HCFC-226cb, HCFC-224aa and HCFC-224ba. Such an isomerized crude liquid is distilled to separate compounds other than HCFC-225, thereby to obtain HCFC-225 containing HCFC-225ca and HCFC-225aa as the main components.

TABLE 2

|  |  | Isomerized crude liquid |
|---|---|---|
| HCFC-225 (mol %) |  | 81.3 |
| Other than HCFC-225 (mol %) | HCFC-226cb | 6.0 |
|  | HCFC-224aa | 0.5 |
|  | HCFC-224ba | 6.2 |
|  | Other compounds | 6.0 |
| Composition of HCFC-225 (mol %) | HCFC-225cb | 1.0 |
|  | HCFC-225ca | 60.0 |
|  | HCFC-225aa | 38.0 |
|  | Other 225 compounds | 1.0 |

203 g of HCFC-225 containing HCFC-225ca and HCFC-225aa as the main components, thus obtained, was charged together with 0.3 g of TBAB, 34 g of potassium hydroxide and 51 g of water, into a glass reactor having an internal capacity of 1 L and provided with a Dimroth condenser cooled to 0° C., and then, a reaction was carried out at 20° C. for 5 hours with stirring to selectively dehydrofluorinate HCFC-225ca.

Then, the obtained crude liquid was subjected to liquid separation, and then, formed CFO-1214ya was distilled and recovered, and further, low boiling point components and high boiling point components were distilled and recovered, to obtain HCFC-225 containing HCFC-225aa as the main component. This HCFC-225 was used as a raw material in Examples 1 to 6 and Comparative Example 1.

And, the temperature of the salt bath was raised to the reaction temperature shown in Table 3, and the above HCFC-225 containing HCFC-225aa as the main component, was passed through the reaction tube under the conditions shown in Table 3 to carry out an isomerization reaction. The reaction was continued for 10 hours, and then, the gas composition at the outlet of the reactor was analyzed by gas chromatography to carry out the compositional analysis of the product. The results are shown in Table 3.

TABLE 3

|  |  | Composition of raw material | Example 1 | Example 2 | Example 3 | Example 4 | Example 5 | Example 6 | Comparative Example 1 |
|---|---|---|---|---|---|---|---|---|---|
| Reaction conditions | Reaction temperature |  | 200° C. | 230° C. | 250° C. | 270° C. | 280° C. | 290° C. | 300° C. |
|  | Raw material-supply ratio HCFC-225/N$_2$ |  | 1/2 | 1/2 | 1/2 | 1/2 | 1/2 | 1/2 | 1/2 |
|  | Contact time |  | 20 sec. | 20 sec. | 20 sec. | 20 sec. | 20 sec. | 20 sec. | 20 sec. |
| HCFC-225 (mol %) |  | 100.0 | 99.0 | 97.0 | 95.9 | 91.3 | 90.4 | 87.9 | 80.0 |
| Other than HCFC-225 (mol %) | HCFC-226cb | 0 | 0.1 | 0.4 | 1.6 | 3.2 | 2.9 | 3.4 | 6.8 |
|  | HCFC-224aa | 0 | 0 | 0.1 | 0 | 0.1 | 0.1 | 0.1 | 0.1 |
|  | HCFC-224ba | 0 | 0.3 | 1.0 | 1.1 | 3.1 | 3.1 | 4.0 | 6.9 |
|  | Other compounds*1 | 0 | 0.6 | 1.5 | 1.4 | 2.3 | 3.5 | 4.6 | 6.2 |
| Composition of HCFC-225 (mol %) | HCFC-225cb | 2.5 | 0 | 0.1 | 0.2 | 0.2 | 0.1 | 0.1 | 0.2 |
|  | HCFC-225ca | 0 | 59.2 | 61.3 | 61.3 | 60.9 | 57.8 | 60.4 | 59.7 |
|  | HCFC-225aa | 95.0 | 40.6 | 38.4 | 38.1 | 37.9 | 38.6 | 35.6 | 37.7 |
|  | Other 225 compounds | 2.5 | 0.2 | 0.2 | 0.4 | 1.0 | 3.5 | 3.9 | 2.4 |

*1HCFC-226 isomers other than HCFC-226cb, and HCFC-224 isomers other than HCFC-224aa and HCFC-224ba, etc.

Examples 7 to 10

To HCFC-225 containing HCFC-225aa as the main component as the raw material used in Examples 1 to 6, HCFC-225cb was mixed to obtain a raw material having the composition shown in Table 4. This raw material was passed through the reaction tube under the conditions shown in Table 4 to carry out an isomerization reaction. The reaction was continued for 10 hours, and then the gas composition at the outlet of the reactor was analyzed by gas chromatography to carry out the compositional analysis of the product. The results are shown in Table 4.

TABLE 4

|  |  | Example 7 | | Example 8 | | Example 9 | | Example 10 | |
| --- | --- | --- | --- | --- | --- | --- | --- | --- | --- |
| Reaction conditions | Reaction temperature | 200° C. | | 250° C. | | 200° C. | | 250° C. | |
|  | Raw material-supply ratio HCFC-225/N$_2$ | 1/2 | | 1/2 | | 1/2 | | 1/2 | |
|  | Contact time | 20 sec. | | 20 sec. | | 20 sec. | | 20 sec. | |
|  |  | Raw material | Product | Raw material | Product | Raw material | Product | Raw material | Product |
| HCFC-225 (mol %) |  | 100.0 | 99.0 | 100.0 | 95.9 | 100.0 | 99.0 | 100.0 | 95.9 |
| Other than HCFC-225 (mol %) | HCFC-226cb | 0 | 0.1 | 0 | 1.6 | 0 | 0.1 | 0 | 1.5 |
|  | HCFC-224aa | 0 | 0 | 0 | 0 | 0 | 0 | 0 | 0 |
|  | HCFC-224ba | 0 | 0.3 | 0 | 1.0 | 0 | 0.3 | 0 | 1.0 |
|  | Other compounds*1 | 0 | 0.6 | 0 | 1.5 | 0 | 0.6 | 0 | 1.6 |
| Composition of HCFC-225 (mol %) | HCFC-225cb | 20.0 | 8.5 | 20.0 | 3.0 | 50.0 | 20.5 | 50.0 | 7.5 |
|  | HCFC-225ca | 0 | 54.0 | 0 | 59.5 | 0 | 47.1 | 0 | 56.7 |
|  | HCFC-225aa | 77.5 | 37.1 | 77.5 | 37.0 | 38.5 | 32.3 | 38.5 | 35.1 |
|  | Other 225 compounds | 2.5 | 0.4 | 2.5 | 0.5 | 1.5 | 0.1 | 1.5 | 0.7 |

Example 11

Using the product (reaction crude liquid) obtained in Example 7, CFO-1214ya was produced by the following method.

That is, into a glass reactor having an internal capacity of 1 L and provided with a Dimroth condenser cooled to 0° C., 3 g of TBAB as a phase-transfer catalyst, 129 g of potassium hydroxide (2.30 mol), 220 g of water and 600 g of the product obtained in Example 7 were charged, and then, a reaction was carried out at 20° C. for 5 hours with stirring, whereby a reaction crude liquid was obtained, wherein an organic phase and an aqueous phase were separated in two phases. A part of the organic phase of the obtained reaction crude liquid was recovered, and the composition was analyzed by gas chromatography. The results are shown in Table 5.

Further, after the analysis of the composition by gas chromatography, the reaction crude liquid was subjected to liquid separation, and the organic phase was charged into a distillation column having a bottom capacity of 1 L and an ability of a theoretical plate number of 10 plates, followed by distillation. As a result of the distillation, it was possible to recover 307 g (1.68 mol) of CFO-1214ya (boiling point: 45° C.) having a purity of 99.5%.

TABLE 5

|  |  | Raw material | Example 11 |
| --- | --- | --- | --- |
| Composition of HCFC-225-(mol %) | HCFC-225cb | 8.5 | 8.5 |
|  | HCFC-225ca | 54.0 | 0 |
|  | HCFC-225aa | 37.1 | 37.0 |
|  | Other 225 compounds | 37.1 | 29.5 |
| Other than HCFC-225 (mol %) | HCFC-226cb | 0.1 | 0.1 |
|  | HCFC-224aa | 0 | 0 |
|  | HCFC-224ba | 0.3 | 0.3 |
|  | CFO-1214ya | 0 | 54.0 |
|  | Other compounds | 0.6 | 0.6 |

From Table 5, it was confirmed that only HCFC-225ca in the raw material was selectively dehydrofluorinated, whereby CFO-1214ya was obtained.

Then, active carbon having palladium supported thereon in a ratio of 2 mass % (tradename: Shirasagi C2X, manufactured by Takeda Pharmaceutical Company Limited.) was packed into a reaction tube made of Inconel 600 and having an inner diameter of 2.54 cm and a length of 100 cm, and was immersed in a salt bath. And, into this reaction tube, CFO-1214ya obtained by the above method was charged, and a reduction reaction was carried out under the reaction conditions shown in the upper section in Table 6. Confirmation of the reaction product was carried out by analyzing an outlet gas from the reactor by gas chromatography and calculating the crude gas composition. The results are shown in the lower section in Table 6.

TABLE 6

| Reaction conditions | Reaction temperature | 200° C. |
| --- | --- | --- |
| | Raw material supply ratio: CFO-1214ya/H$_2$/N$_2$ | 1/1/2 (molar ratio) |
| | Contact time | 53 seconds |
| Crude gas composition | CF$_3$CF=CCl$_2$ (CFO-1214ya) | 0 mol % |
| | CF$_3$CF=CH$_2$ (HFO-1234yf) | 72 mol % |
| | Other compounds | 28 mol % |

From Table 6, it was confirmed that all amount of CFO-1214ya was reduced, and HFO-1234yf was obtained in good yield.

INDUSTRIAL APPLICABILITY

According to the present invention, it is possible to obtain HCFC-225ca in a high content ratio. The obtained HCFC-225ca is useful, for example, as a starting material for producing CFO-1214ya useful as a raw material for synthesis of HFO-1234yf which is a new refrigerant.

The entire disclosures of Japanese Patent Application No. 2010-142278 filed on Jun. 23, 2010 and U.S. Provisional Application No. 61/365,919 filed on Jul. 20, 2010 including specifications, claims and summaries are incorporated herein by reference in their entireties.

What is claimed is:

1. A process for producing 1,1-dichloro-2,2,3,3,3-pentafluoropropane, which comprises reacting a raw material comprising 2,2-dichloro-1,1,1,3,3-pentafluoropropane at a temperature of 150° C. to 290° C. in a gas phase in the presence of a metal oxide catalyst thereby to isomerize at least a part of 2,2-dichloro-1,1,1,3,3-pentafluoropropane in the raw material to 1,1-dichloro-2,2,3,3,3-pentafluoropropane.

2. The process for producing 1,1-dichloro-2,2,3,3,3-pentafluoropropane according to claim 1, wherein the raw material further contains 1,3-dichloro-1,2,2,3,3-pentafluoropropane, and in the above reaction, at the same as isomerization of 2,2-dichloro-1,1,1,3,3-pentafluoropropane to 1,1-dichloro-2,2,3,3,3-pentafluoroporpane, at least a part of the 1,3-dichloro-1,2,2,3,3-pentafluoropropane is isomerized to 1,1-dichloro-2,2,3,3,3-pentafluoropropane.

3. The process for producing 1,1-dichloro-2,2,3,3,3-pentafluoropropane according to claim 1 or 2, wherein the temperature for the reaction is at least 150° C. to 180° C.

4. The process for producing 1,1-dichloro-2,2,3,3,3-pentafluoropropane according to claim 1 or 2, wherein the metal oxide catalyst is an aluminum oxide type catalyst.

5. The process for producing 1,1-dichloro-2,2,3,3,3-pentafluoropropane according to claim 1 or 2, wherein the above metal oxide catalyst is a partially fluorinated metal oxide catalyst.

6. The process for producing 1,1-dichloro-2,2,3,3,3-pentafluoropropane according to claim 1 or claim 2, wherein the metal oxide catalyst is a partially fluorinated aluminum oxide catalyst.

7. The process for producing 1,1-dichloro-2,2,3,3,3-pentafluoropropane according to claim 1 or claim 2, wherein hydrochlorofluorocarbon compounds other than dichloropentafluoropropane, which are produced as by-products are less than 10 mol % based on the total amount of dichloropentafluoropropane in the reaction product.

8. A process for producing 1,1-dichloro-2,2,3,3,3-pentafluoropropane, which comprises:
subjecting dichloropentafluoropropane containing 1,1-dichloro-2,2,3,3,3-pentafluoropropane and 2,2-dichloro-1,1,1,3,3-pentafluoropropane to a dehydrofluorination reaction in an alkali aqueous solution in the presence of a phase-transfer catalyst to produce 1,1-dichloro-2,3,3,3-tetrafluoropropene from 1,1-dichloro-2,2,3,3,3-pentafluoropropane;
then, separating 1,1-dichloro-2,3,3,3-tetrafluoropropene from the reaction product; and
reacting dichloropentafluoropropane containing 2,2-dichloro-1,1,1,3,3-pentafluoropropane after separating 1,1-dichloro-2,3,3,3-tetrafluoropropene, at a temperature of 150° C. to 290° C. in a gas phase in the presence of a metal oxide catalyst thereby to isomerize at least a part of 2,2-dichloro-1,1,1,3,3-pentafluoropropane in the above dichloropentafluoropropane to 1,1-dichloro-2,2,3,3,3-pentafluoropropane.

9. A process for producing 1,1-dichloro-2,3,3,3-tetrafluoropropene, which comprises:
subjecting dichloropentafluoropropane containing 1,1-dichloro-2,2,3,3,3-pentafluoropropane and 2,2-dichloro-1,1,1,3,3-pentafluoropropane to a dehydrofluorination reaction in an alkali aqueous solution in the presence of a phase-transfer catalyst to produce 1,1-dichloro-2,3,3,3-tetrafluoropropene from 1,1-dichloro-2,2,3,3,3-pentafluoropropane;
separating 1,1-dichloro-2,3,3,3-tetrafluoropropene from the above dehhydrofluorination reaction product;
reacting dichloropentafluoropropane containing 2,2-dichloro-1,1,1,3,3-pentafluoropropane after separating 1,1-dichloro-2,3,3,3-tetrafluoropropene, at a temperature of 150° C. to 290° C. in a gas phase in the presence of a metal oxide catalyst, to isomerize a part of 2,2-dichloro-1,1,1,3,3-pentafluoropropane in the above dichloropentafluoropropane thereby to produce dichloropentafluoropropane including 1,1-dichloro-2,2,3,3,3-pentafluoropropane and 2,2-dichloro-1,1,1,3,3-pentafluoropropane; and
repeating the above process to produce 1,1-dichloro-2,3,3,3-tetrafluoropropene from the obtained dichloropentafluoropropane.

10. The process for producing 1,1-dichloro-2,3,3,3-tetrafluoropropene according to claim 9, wherein the above isomerization reaction is carried out by adding 1,3-dichloro-1,2,2,3,3-pentafluoropropane to the dichloropentafluoropropane as the raw material for the isomerization reaction, so that at the same time as the isomerization of 2,2-dichloro-1,1,1,3,3-pentafluoropropane to 1,1-dichloro-2,2,3,3,3-pentatluoropropane, the 1,3-dichloro-1,2,2,3,3-pentafluoropropane is isomerized to 1,1-dichloro-2,2,3,3,3-pentafluoropropane.

11. The process for producing 1,1-dichloro-2,3,3,3-tetrafluoropropene according to claim 9 or 10, wherein the isomerization reaction is carried out by adding 2,2-dichloro-1,1,1,3,3-pentafluoropropane to the dichloropentafluoropropane as the raw material for the isomerization reaction.

* * * * *